(12) United States Patent
Ivri

(10) Patent No.: US 9,375,739 B2
(45) Date of Patent: Jun. 28, 2016

(54) PRESSURE MULTIPLYING AEROSOL PUMP

(71) Applicant: Yehuda Ivri, Newport Coast, CA (US)

(72) Inventor: Yehuda Ivri, Newport Coast, CA (US)

( * ) Notice: Subject to any disclaimer, the term of this patent is extended or adjusted under 35 U.S.C. 154(b) by 0 days.

(21) Appl. No.: 14/197,487

(22) Filed: Mar. 5, 2014

(65) Prior Publication Data

US 2014/0252128 A1 Sep. 11, 2014

Related U.S. Application Data

(60) Provisional application No. 61/963,421, filed on Dec. 3, 2013, provisional application No. 61/962,953, filed on Nov. 19, 2013, provisional application No. 61/960,072, filed on Sep. 9, 2013, provisional application No. 61/851,415, filed on Mar. 7, 2013.

(51) Int. Cl.
*B05B 11/02* (2006.01)
*B05B 11/00* (2006.01)

(52) U.S. Cl.
CPC ......... *B05B 11/3005* (2013.01); *B05B 11/3052* (2013.01)

(58) Field of Classification Search
CPC ............ B05B 11/3001; B05B 11/3087; B05B 11/3088; B05B 11/3005; B05B 11/3042; B05B 11/3052
USPC .................................. 239/329, 331, 332, 333
See application file for complete search history.

(56) References Cited

U.S. PATENT DOCUMENTS

| 3,933,279 A | 1/1976 | Maier | |
|---|---|---|---|
| 4,197,994 A * | 4/1980 | Liedberg | 239/61 |
| 4,200,204 A | 4/1980 | Bauer et al. | |
| 4,396,152 A | 8/1983 | Abplanalp | |
| 4,925,101 A * | 5/1990 | Konieczynski | B05B 1/262 239/124 |
| 2011/0000980 A1 | 1/2011 | Yamamoto et al. | |
| 2012/0031419 A1 | 2/2012 | Batt et al. | |

FOREIGN PATENT DOCUMENTS

WO PCT/US2014/020687 6/2014

OTHER PUBLICATIONS

DuPont™ Dymel® Aerosol Propellants, Technical Information ATB-29, Dymel® 152a Hydrofluorocarbon 152a, Fluorochemicals Laboratory E.I. DuPont Nemours and Company, 5 pages, 2011, https://www.chemours.com/Dymel_Propellants/en_US/assets/downloads website.

* cited by examiner

*Primary Examiner* — Christopher Kim

(57) ABSTRACT

A hand-held dispensing device operable to dispense a fluid as an atomized spray by hydraulic pressure. The device includes a cartridge containing a fluid to be dispensed and a pressure-multiplying piston pump operable by liquefied gas pressure and manually controlled by a valve. The pump is configured to receive pressure from a compartment containing liquefied gas and transmit higher pressure to the fluid to be dispensed. The pressure multiplying pump produces high pressure, typically between 6-30 bar, which is suitable for generation of fine spray by hydraulic atomization. The device uses about $\frac{1}{10}^{th}$ the amount of liquefied gas compared to a propellant-based aerosol therefore it has a significant ecological and health benefits.

19 Claims, 11 Drawing Sheets

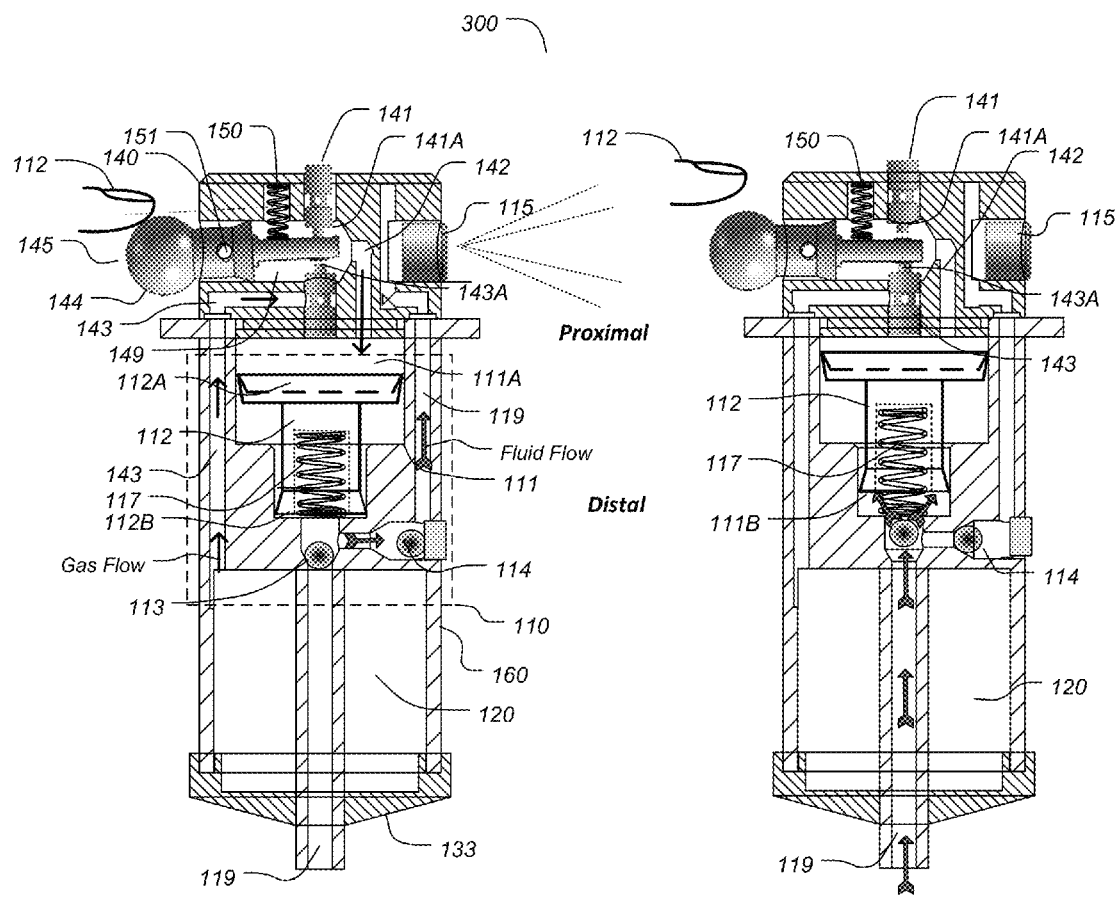
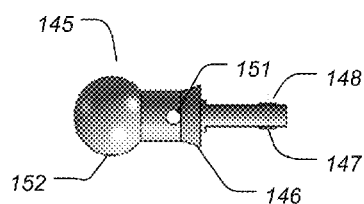
FIG.3A  FIG.3B
Fig.3C

SECTION A-A

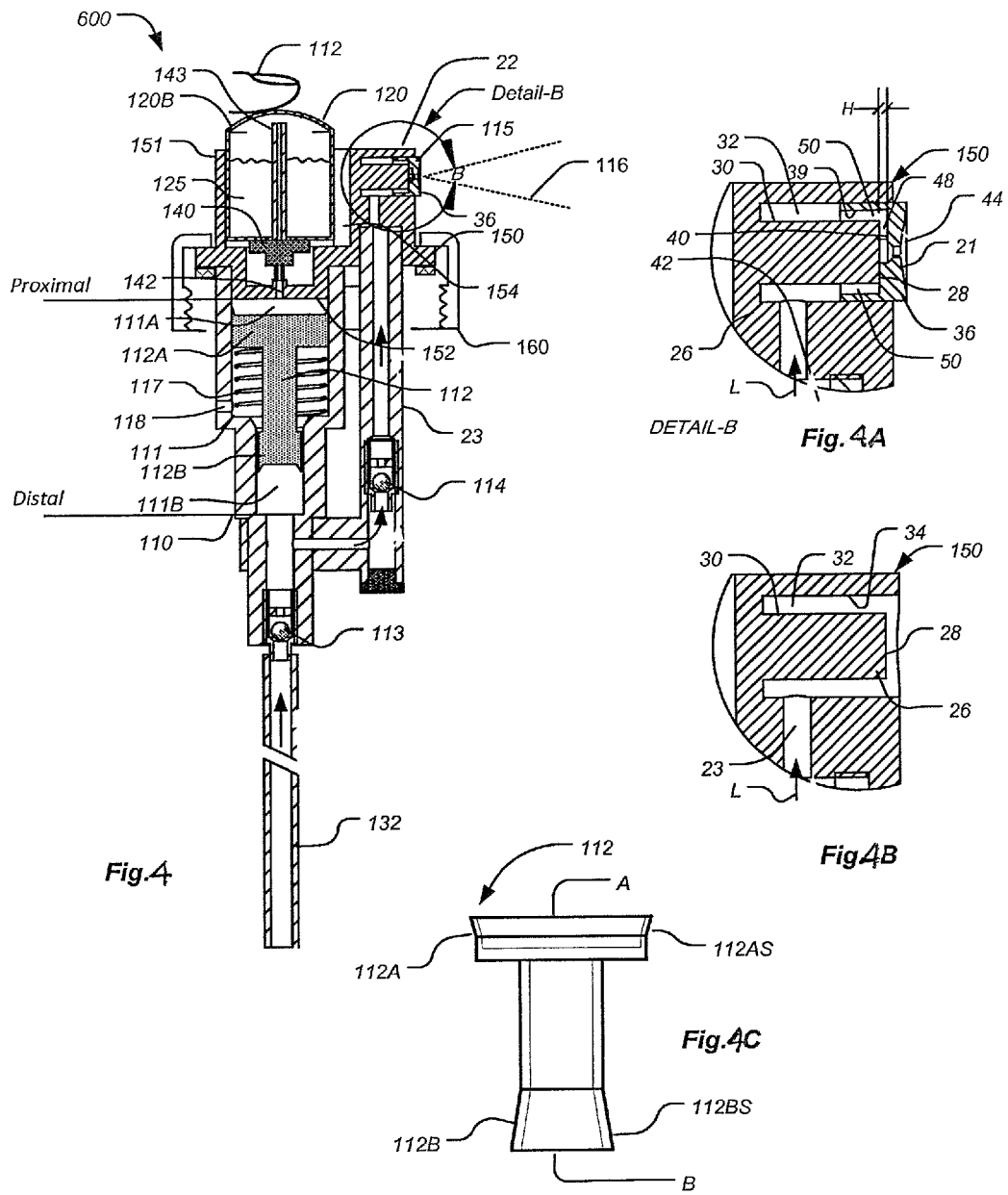

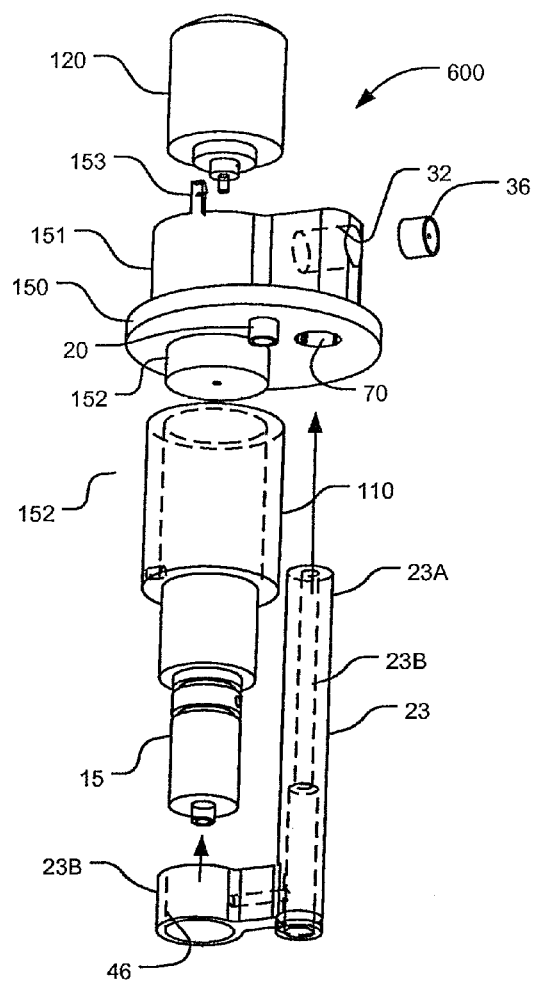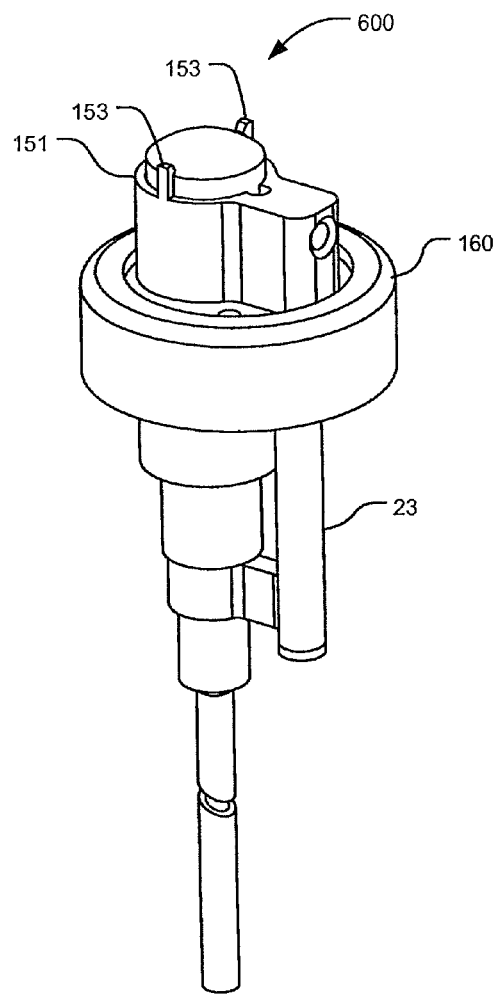
Fig.4D                    Fig.4E

PRESSURE MULTIPLYING AEROSOL PUMP

CROSS-REFERENCE TO RELATED APPLICATIONS

This patent application claims priority to U.S. Provisional Patent Application Ser. No. 61/851,415, filed on Mar. 7, 2013, entitled Propellant Actuated Piston Pump for Handheld Dispensers and U.S. Provisional Patent Application Ser. No. 61/960,072, entitled Gas Actuated Piston Pump for Handheld Dispensers filed on Sep. 9, 2013, and U.S. Provisional Patent Application Ser. No. 61/962,953, filed on Nov. 19, 2013, entitled Pressure Multiplying Aerosol Pump and 61/963,421, filed on Dec. 3, 2013, entitled Pressure Multiplying Aerosol Pump, the entirety of each one is hereby incorporated by reference herein.

BACKGROUND OF THE INVENTION

Hand held spray dispensers are typically either of the manually-actuated spray pump type or the aerosol spray type. Aerosol spray dispensers utilize a liquefied gas propellant that "flashes off", to create a fine spray. These ultra fine sprays have mean droplet diameters on the order of about 40 microns. Such a spray characteristic is desirable in many applications in cosmetics and industrial coatings. This sprayer however has several disadvantages. The composition contains a large volume of liquefied gas and other volatile organic compounds (VOCs) which are known to react with certain nitrogenic oxides ($NO_x$), which in turn may result in the formation of ground-level ozone—a potential source of health problems. Certain propellants such as hydrocarbons and hydro-fluorocarbons gases also contribute to global warming. Therefore, there are ecological pressures to reduce, or avoid entirely, the use of VOCs in aerosol products.

Manually-actuated spray pump dispensers or finger pumps rely on the consumer to generate a hydraulic pressure in the pumping engine in order to dispense the fluid. Most pumping engines typically use a standard piston and cylinder arrangement to generate hydraulic pressure. When the consumer applies an actuation force by pushing downward on the piston, the hydraulic pressure of the fluid in the cylinder is increased. Most manually-actuated spray pump dispensers have been unable to produce sprays having a mean droplet diameter of less than about 55 microns. These larger mean particle sizes, produced by conventional manual spray pumps is too coarse for many applications. These larger particle sizes result in sprays that users refer to as "wet".

Most conventional spray pumps operate at a hydraulic pressure of about 6 bar. Research has indicated that when the hydraulic pressure in these conventional spray pumps is increased upward to levels near about 14 bar, mean droplet diameters of about 40 microns or less are achievable.

A method of developing a high hydraulic pressure of about 14 bar requires actuation force from about 44 Newton to about 88 Newton. An actuation forces in this range is too excessive for most consumers to attain by manual pumping. Such an actuation force can quickly fatigue the finger and hand of even the most physically adept person, let alone the typical users of most finger pumps.

A need exists for an aerosol propellant method that is capable of delivering substantially higher hydraulic pressures to create a fine spray driven by aerosol created pressure while reducing the ecological problems associated with existing aerosol propellant dispensers.

The present invention provides a new dispensing device and dispensing method that produces 14 bar of pressure for dispensing liquid in a fine spray. The device comprises a spring-loaded piston member and valve system similar to that in a finger-triggered spray pump. The activation force however is generated by the expansion of liquefied gas stored in a small gas compartment within the pump. The piston is configured to multiply the gas pressure and transmit higher pressure to the fluid composition in the nozzle. It has been found that the amount of liquefied gas that is needed is about $\frac{1}{10}^{th}$ when compared to propellant-based aerosol that produces the same aerosol characteristics.

SUMMARY OF THE INVENTION

The present invention is directed to a hand-held dispensing device operable to dispense fluids in a spray of fine particles by hydraulic pressure. The device includes a cartridge containing a fluid to be dispensed and a pressure-multiplying piston pump actuated by liquefied gas pressure and manually controlled by a gas valve. The pump is configured to receive pressure from a compartment containing liquefied gas and transmit higher pressure to the fluid to be dispensed. The pressure multiplier produces high pressure, typically between 6-30 bar, which is suitable for generation of fine spray by hydraulic atomization. The device uses about $\frac{1}{10}^{th}$ the amount of liquefied gas propellant, as compared to a propellant-based aerosol. It has substantial ecological benefits in relation to air pollution and release of greenhouse gases.

The term propellant-based aerosol means a dispensing device that contains a volatile composition of liquefied gas and active fluid that is dispensed through a nozzle and rapidly dispersed as a fine aerosol. Such propellant-based aerosol devices are described, for example in U.S. Pat. No. 3,207,386, U.S. Pat. No. 3,948,817, U.S. Pat. No. 4,254,104, U.S. Pat. No. 4,444,745, U.S. Pat. No. 4,536,323, and EP 0155697.

The dispensing device of the present invention includes a cartridge containing fluid to be dispensed and a gas-actuated pressure-multiplying piston pump. The pump is connected to a source of pressure and controlled by a manually operated 3-way 2-position gas valve. The gas is stored in a separate compartment in a liquefied state. The piston is configured to amplify or multiply the gas pressure such that the pressure that is transmitted to the fluid is sufficient to produce an aerosol of fine particles by hydraulic atomization.

It has been found that the quantity of liquefied gas that is required to dispense a volume of liquid at a given fine particle size using the embodiment of present invention is much smaller than the amount of liquefied gas needed to dispense the same fluid at the same particle size with a commonly used propellant-based composition.

Commonly used propellants in cosmetic, household product and other aerosol coating products include volatile organic compounds (VOCs) such as propane, butane, 1,1-difluoroethane, and dimethylether. These VOCs are known to react with certain nitrogenic oxides ($NO_x$), which in turn may result in the formation of ground-level ozone—a potential source of health problems. Maximum incremental reactivity (MIR) is a measure of the ozone-forming potential of a compound and there are pressures to keep the calculated MIR value of products as low as possible. (For example: Regulation for Reducing the Ozone Formed for hairspray and Aerosol Coating—State of California). There are ecological pressures to reduce, or avoid entirely, the use of VOCs in cosmetic, household and in other industrial products.

The pressure-multiplier piston pump comprises a cylinder member and a spring-loaded piston member. The cylinder member includes a body with two unequal cylinder bores wherein with first cylinder bore has a larger diameter than the second cylinder bore. The spring-loaded piston member comprises two integrally connected pistons wherein the diameter of the first piston is equal to the diameter of first cylinder bore and the diameter of the second piston is equal to the diameter of the second cylinder bore. The spring-loaded piston member is arranged to travel inside the cylindrical member.

The first large piston is in pressure communication with gas pressure source through a control valve. The second piston is in fluid communication with the fluid to be dispensed. The first piston has a larger diameter than the second piston. The pressure that is transmitted to the fluid increases in proportion to the areas of the pistons. High pressure is used to dispense fluid as an atomized spray or to dispense high viscosity fluids in the form of a spray, a stream, a jet, or the like.

Preferably, the pressure generated by the smaller piston is at least 10 bar, and more preferably 15 bar, and even more preferably 20, 25, 30 or 35 bar. The maximum pressure will typically be less than 50 bar.

The ratio between the area of the large piston and the small piston is preferably greater than 1, 2, 3 or 4, but typically less than 10.

The term hydraulic atomization means that the fluid to be atomized is pressurized by the displacement of a piston and discharged to the atmosphere through an atomizing nozzle.

A nozzle that is commonly used in hydraulic atomization and can be used in the dispensing device of the present invention is a pressure-swirl nozzle. Such a nozzle induces a spinning motion to the fluid prior to it exiting to the atmosphere. The spray that is discharged from a pressure-swirl nozzle breaks into fine fluid droplets. Higher pressure generally produces finer droplets. Alternatively, an aperture plate containing a multiplicity of small apertures may also be used. Such an aperture plate is commonly made by a process of nickel electroforming. Such an aperture plate may contain a dense array of apertures, typically between 500-5000 apertures. The exit diameter of 5 each aperture is typically between 6-20 microns. The thickness of the aperture plate is preferably between 75-100 microns.

Electroforming manufacture process produces apertures in a plate that have flared or conical shape holes that have a low discharge coefficient.

The liquefied gas is selected from a group of hydrocarbon, hydro-fluorocarbon, unsaturated fluorocarbon or hydrofluoroolefin. Preferably the selected gas has low Global Warming Potential (GWP), less than 150, 130, 120 100, 50 and most preferably less than 6. Preferably, the liquefied gas will have low MIR value and is not considered a VOC by government agencies such as the United States Environmental Protection Agency (EPA). Preferably, the liquefied gas is not flammable.

Liquefied gases that have such properties are hydro-fluorocarbon such as Dymel™ HFA-152a, Ethane, DME (di-mathyl ether) and particularly HF0-1234ze. In some cases a blend of hydrocarbon, unsaturated fluorocarbon or hydrofluorocarbon may also be used. For example, 88% HF0-1234ze and 12% Ethane may be used to alter the vapor pressure and the degree of flammability. The above mentioned composition has a vapor pressure of 108 psi. Alternative blend of 50% HF0-1234ze and 50% i HFC-152a may also be used. Such blend has lower flammability than HFC-152a. The concentration of HF0-1234ze may be 100, 88, 80, 70, 60, 50, 40, 30, 20 percent and the balance maybe any hydrocarbon gas including ethane, or hydro-fluorocarbon specifically HFA-152a.

Various blends that can be used in the dispensing device of the present invention are disclosed in the publication titled "Propellant and Solvent 2012 and Beyond Strategies for the 21$^{st}$ Century Published by Southern Aerosol Inc. and in "An Introduction to Aerosol Propellant" published by Diversified CPC International, Inc." Both documents are incorporated here by reference.

The dispensing system further includes a control valve which controls the supply of gas pressure or atmospheric pressure to the pump. The valve can switch between the gas pressure port and the atmospheric pressure port. At a normal position the valve is connected to the atmospheric pressure port and the spring-loaded piston is biased by a spring to one end of the cylinder. In a second position the valve is connected to the gas pressure port and the piston is displaced to the opposite end of the cylinder while compressing the spring and dispensing fluid. When the control valve is switched back to atmospheric pressure the gas is released to the atmosphere and the piston returns by its spring to the normal position while drawing more fluid from the container.

The control valve switches between the gas pressure port and atmospheric pressure port by finger actuation or the like.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 3A is a cross sectional view of the pressure multiplying dispensing system showing the position of the piston, the valves and the direction of fluid flow when the control valve is pressed.

FIG. 3B is a cross sectional view of the pressure multiplying dispensing system showing the position of the piston, the valves and the direction of fluid flow when the actuation valve is released.

FIG. 3C is a detail view of a rocker arm actuator.

FIG. 4 is a simplified cross sectional view of pressure-multiplying dispensing system in accordance with certain embodiments of the invention.

FIG. 4A illustrates enlarged cross sectional views of pressure swirl nozzle shown as Detail B of FIG. 6.

FIG. 4B illustrates enlarged cross sectional views FIG. 4A without the pressure swirl nozzle.

FIG. 4C is a detail view of certain pressure-multiplying piston.

FIG. 4D illustrates an exploded view that best shows the interconnection between external components in accordance with certain embodiments of the invention.

FIG. 4E illustrates a perspective view that best shows the interconnection between external components system in accordance with certain embodiments of the invention.

DETAILED DESCRIPTION OF THE INVENTION

Figure 1:
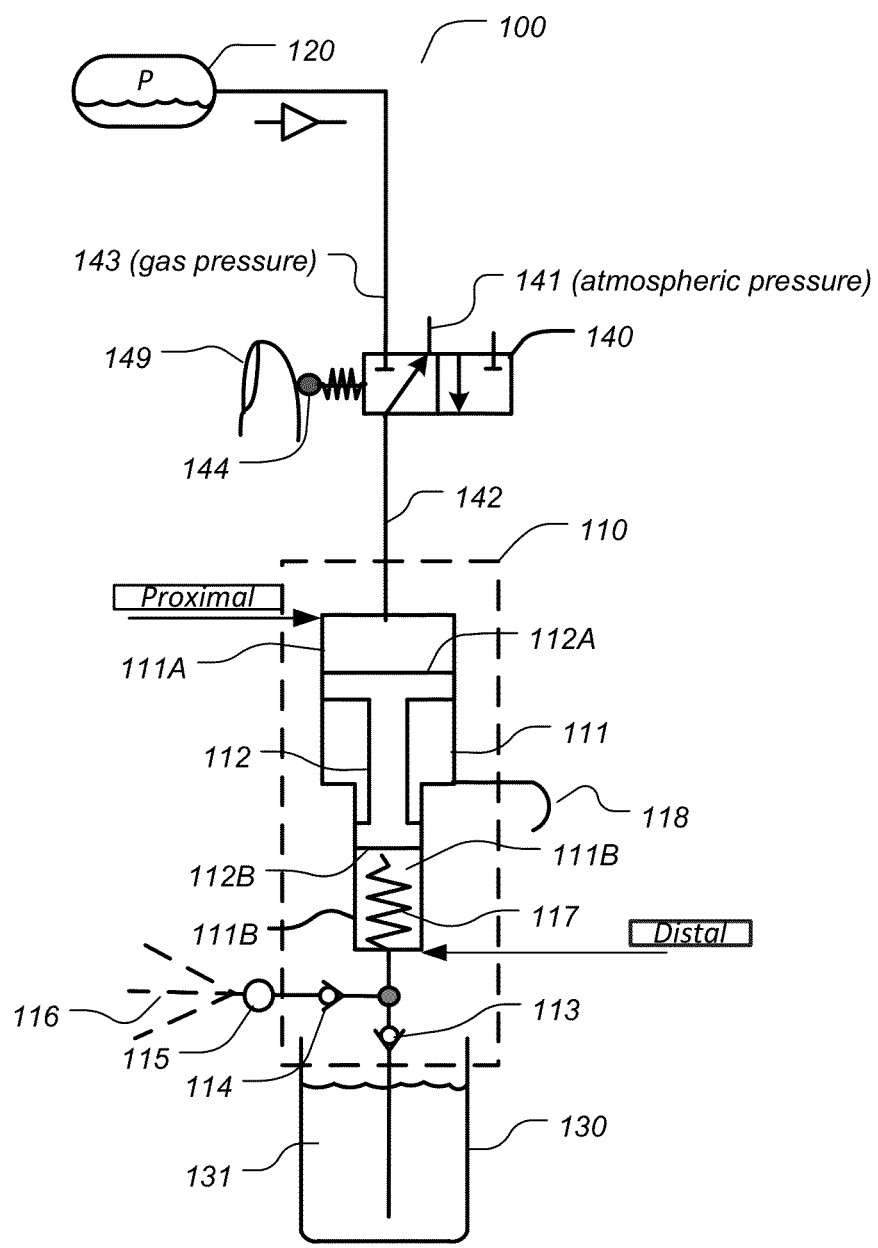
FIG. 1 is a simplified schematic view of the pressure multiplying dispensing system illustrating the main building blocks in accordance with the present invention.

FIG. 1 illustrates a schematic diagram in accordance to an exemplary embodiment of dispensing system (100). Dispensing system (100) includes a pressure-multiplying pump (110) operable by liquefied gas pressure from a separate pressure container (120) manually controlled by valve (140). Dispensing system (100) is configured to draw fluid (131) from a separate container (130) and dispenses it through a nozzle (115) as an atomized spray (116) at a pressure that is greater than the gas pressure L in pressure container 120.

Pressure-multiplying pump (110) includes a cylinder body (111) which contains a spring-loaded piston member (112). When pressure P is applied to (111A) of cylinder (111), spring-loaded piston (112) is displaced from the proximal to the distal end of cylinder (111) compressing spring (117). When the pressure on cylinder surface (112A) is exhausted to the atmosphere spring-loaded piston (112) returns by the force of spring (117) to the proximal end of cylinder (111). The movement of the piston from the distal end to the proximal end draws fluid (131) from the container (130) into cylinder (111B). Movement in the reverse direction dispenses the fluid (131) through nozzle (115). A pair of check valves (113) and (114) restrict movement of fluid (131) from the container (130) to nozzle (115).

Pressure multiplying pump (110) is arranged to amplify the gas pressure P and transmit a higher pressure to fluid (131). Cylinder (111) has a stepped bore with a large diameter portion (111A) at its proximal end and a small diameter portion (111B) at its distal end. Accordingly spring-loaded piston member (112) includes a pair of axially-connected pistons (112A) and (112B) that diametrically match cylinders (111A) and (111B) respectively. In this way the gas pressure P that is applied to cylinder (111A) produces higher fluid pressure in cylinder (111B). The fluid pressure produced is equal to the arithmetic product of the gas pressure P and the ratio between the areas of pistons (112A) and (112B). This high pressure may be used to effectively atomize fluid or dispense a flowable viscous fluid. Fluids with high viscosity up to 50,000 cP or even 100,000 cP may be dispensed in this way.

The pressure multiplier of the present invention is configured to increase the gas pressure and transmit higher pressure to the fluid composition at the nozzle. The actual pressure is also dependent on pressure loss at the nozzle (115). Preferably, nozzles with a low discharge coefficient will be used, such as those described in U.S. Patent Publication 2006/0275220 and U.S. Pat. No. 5,711,488.

Cylinder (111) includes a venting port (118) near the junction between cylinder (111A) and (111B) to prevent compression of the air between piston (112A) and (112B).

Valve (140) controls the operation of dispensing unit (100) by switching the connection of pump inlet port (142) to either gas pressure port (143) or to exhaust port (141). At the normal rest position pump inlet port (142) is connected to the exhaust port (141) and piston (112) is biased by the spring (117) to the proximal end of the cylinder (111). At the "on" position pump inlet port (142) is connected to gas pressure port (143) and the piston is displaced to the distal end of the cylinder compressing spring (117). When control valve (140) is switched back to normal rest position, piston (112) returns by spring (116) to the proximal position. The reciprocating movement of piston (112) moves the fluid to be dispensed from container (130) and dispenses it through nozzle (115) at a pressure that is greater than the gas pressure P.

In one embodiment the diameter of piston (112A) is 12 mm and the diameter of piston (112B) is 6 mm. The resulting area of the first piston (112A) is 113 mm$^2$ and the area of piston (1128) is 28.2 mm$^2$. The ratio between the areas of the two pistons is about 4. The pressure that is applied to the fluid (131) by piston (1128) is approximately 4 times higher than the gas pressure P. Due to friction forces between the piston and the cylinder, the opposing spring force, and pressure loss at the nozzle, the actual pressure may be lower, typically up to 20% lower.

Spring (118) is configured to move piston (112) from the distal to the proximal end of the cylinder during the fluid from the container (130) into the cylinder (1118). This is conveniently fast so that the user does not have to wait more than a fraction of a second between actuation, preferably not longer than 100-400 msec.

In a preferred embodiment the liquefied gas stored in gas compartment (120) is DYMEL™HFC-152A manufacture by DuPont Company Wilmington, Del. (CAS Number 75-37-6). DYMEL™ HFC-152a has a vapor pressure of 4.16 bar at 20 Deg C. Therefore the pressure that is transmitted to the fluid (131) in the cyloinder (111B) is 16.6 bar, 4 times higher than the gas pressure. Such a pressure effectively produces fine droplets with droplets size of 40 microns. The amount of DYMEL™ HFC-152a that is needed to atomize 1 cubic-centimeter of fluid at 16.6 bar is only 0.0451 grams. Therefore the ratio between the weight of the gas and the liquid is 1/0.0451 or 4.51% by weight. In comparison, the percentage weight of liquefied gas in a conventional propellant-based aerosol is about 20%-35% by the total weight of the composition (Ref: Cosmetic and Toiletry Formulation by Ernest Flick).

The dispensing method of the present invention substantially reduces the amount of liquefied gases that are required to dispense a liquid in a fine aerosol type spray and therefore has ecological and health benefits.

Fluid container (130) may contain at least 35, and up to 1000 ml of fluid. Typically it will be less than 2000 ml. Preferably the container is made of plastic material such as polypropylene, PET or PE.

Dispensing system (100) may be used to dispense aerosols of cosmetic compositions such as deodorant or hairspray. U.S. patent publication 2006/0275220 shows models of liquid cosmetic compositions which may be atomized by high hydraulic pressure. Such cosmetic compositions are shown in Table 1 of the above patent publication. Table 2 of the above publication shows the droplets size (Dv, 0.5) as a function of nozzle pressure for the compositions in Table 1.

In can be seen that excellent spray quality is attainable by use of high pressure with the appropriate nozzle system. Patent publication 2006/0275220 entitled "A Method of Creating Cosmetic Spray", is hereby incorporated by reference.

FIG. 2 illustrates an exemplary embodiment of a dispensing unit (200) which includes a fluid container (130), a threaded locknut (135) which includes a gasket (133) for hermetically sealing dispensing unit (200) to container (130) and a dip-tube (132) for drawing the liquid from the container.

Preferably the container will include a standard S.P.I neck finish thread with a nominal diameter of 13 to 75 mm and with type 400, 410 or 415 continuous threads. The container is made of plastic material that is commonly used for packaging fluid. Standard materials will include high-density-polyethylene (HDPE), post consumer resin (PCR), low-density-polyethylene (LDPE), polypropylene (PP), K-Resin Polyvinyl Chloride (PVC), PETG or PET.

Figure 2A:
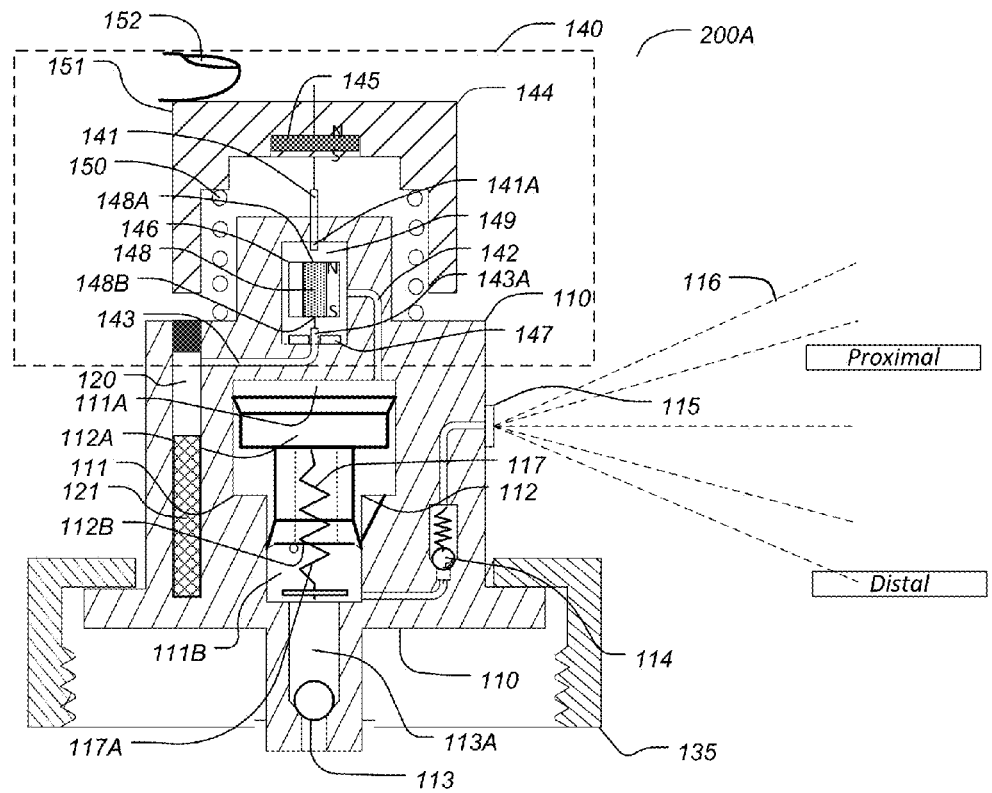
FIG. 2A is simplified enlarged cross sectional view of the pressure multiplying dispensing system shown in FIG. 2.
Figure 2:
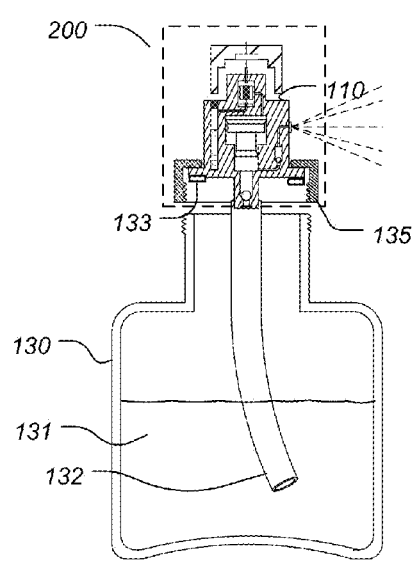
FIG. 2 is a simplified cross sectional view of pressure-multiplying dispensing system in accordance with certain embodiments of the invention.

FIG. 2A is a cross sectional view of dispensing unit (200A) which includes a pressure multiplying pump (110), a gas compartment (120), and a control valve (140) (bounded by dashed line).

Pressure multiplying pump (110) comprising a stepped cylinder bore (111) and reciprocating piston member (112) which includes a pair of axially-connected pistons (112A) and (112B). The pistons are arranged to slide along the axis of the cylinders (111A) and (111B) while maintaining a hermetically tight sealing interference. This arrangement is configured to multiply the gas pressure as described earlier in relation to dispensing unit (100).

In one preferred embodiment the diameter of piston (112A) is 12 mm and the diameter of piston (112B) is 6 mm. Thus, the area of the first piston (112A) is 113 mm$^2$ and the area of piston (112B) is 28.2 mm$^2$. The ratio between the area of two pistons is about 4. The nominal pressure that is applied to the fluid by piston (112B) is 4 times higher than the gas pressure. The liquefied gas stored in chamber (120) is Dymel™ HFC-152A which has a vapor pressure of 4.3 bar at 20° C. Therefore the pressure that is applied to the fluid by piston (112B) is about 17.3 bar. Such pressure is suitable for dispensing viscous material or to dispense spray of very fine particles, typically smaller than 40 microns.

The actual pressure may be about 10% to 15% lower than the calculated pressure due to friction between the piston and the cylinder wall, the force of the spring (117) and the pressure loss at dispensing nozzle (115).

The displacement of piston (112) is about 10, 20, 30, 40, or 50 mm but typically less than 100 mm. Thus, the corresponding dispensing volume may be 0.282, 0.564, 0.846, 1.128 or 1.41 ml but typically less than 4 ml or 6 ml. Higher volumes require less actuations, therefore allowing more convenient operation which may be preferred for certain applications, such as air freshener, hairspray, body deodorant or the like.

Dispensing unit (200A) further includes a gas compartment (120) which contains liquefied gas. Gas compartment (120) defines an annular cavity in a concentric relationship to the cylinder bore (111). The annular cavity defines a partial circular cutout around the cylinder bore (111). The gas cavity (120) revolves about 175 degrees in the clockwise and counterclockwise directions relative to the sectional view shown in FIG. 2A. This partial annular cavity leaves about degrees of angular space for the valve (113) and nozzle (115). Preferably the gas cavity is geometrically configured to form a uniform wall thickness within housing (110) and the cylinder cavity (111). Even wall thickness is preferable in plastic molding processes.

Liquefied gas is stored in the annular gas compartment (120) within a porous polyethylene member (121). Porous member (121) holds the liquefied gas in place regardless of the orientation of dispensing unit (200A). Suitable porous members will have about 40, 50, 60 or 70 percent porosity relative to the total volume of the member. The total volume of the liquefied gas is calculated using the ideal gas law based on pressure multiplication and the total volume of liquid to be dispensed.

Pistons (112) are loaded by a spring (117) which is configured to displace piston (112) from the distal to the proximal end of the piston travel. Spring (117) has sufficient force to displace the piston from the distal end to the proximal end within 100, 200, 300 msec. Excessive spring force reduces the pressure that is transmitted to the fluid. Similar spring-loaded pistons are commonly used in finger-trigger pumps such as Calmar model HF-20325 or HF-16398 or HF-20826 or Seaquist model HF-18551 or HF-21223 or HF-19766. All are distributed by McKeman Packaging, Reno, Nev. USA. In one embodiment the first 3 or 4 spring coils (117A) has a reduced external diameter which serves to keep ball (113) within the valve (113A), preferably at 1-3 mm away from valve seat.

The description of the spring (117) and other component that arc commonly used in finger-trigger piston pump are not intended to he exhaustive since they are very well known by those skilled in the art. This also includes, check valve (113), piston skirt sealing methods, material selection and the like. Modifications or variations of these components are possible and contemplated in light of the above teachings.

Check valve (113) includes a floating ball having a diameter of 3 mm configured to seal a 60 deg. valve seat. The ball is restricted to float between the valve seat and the seat of spring (117). This arrangement is normally employed in finger-triggered pumps such as those described above.

Valve (140) has a cylindrical cavity (149) which includes two orifices. The first orifice (143A) is connected to gas pressure port (143). The second orifice (141A) is connected to the exhaust port (141). Cylindrical cavity (149) further includes a passageway (142) which extends from the cavity to the cylinder (111A). The valve further includes a plunger (146) that is configured to move axially between the two orifices within the cavity (149) such that end-faces (148A) or (1488) of plunger (146) selectively seals, either the first, or the second orifice.

Plunger (146) is made of cylindrical neodymium magnet which is polarized in the axial directions. Cavity (149) further includes a ferromagnetic iron washer (147) seated at the end of the cavity and configured to magnetically pull plunger (146) toward the gas pressure orifice (143A). In this way end face (1488) shuts the gas pressure orifice (143A). Valve (140) further includes a moveable magnetic disk (145) operable to defeat the magnetic attraction between plunger (146) the ferromagnetic disk (147). When magnetic disk (145) is moved to a close proximity from the magnetic plunger (146) the plunger is then pulled away to the opposite end of the cavity thereby closing the exhaust orifice (141A) and opening the pressure orifice (143A), consequently, gas flows from (143A) through passageway (142) to cylinder (111A) and displaces piston (112) to the distal end of cylinder (111) as described earlier in relation to the preferred embodiment (100).

In one embodiment plunger (146) has a cylindrical body with an outside diameter of 5 mm and an inside diameter of 1.5 mm. An elastomeric member (148) facilitates hermetic closure of the orifices. Elastomeric member (148) is made of FKM, EPDM or silicon rubber.

Magnetic disk (145) is seated in a spring-loaded knob (151) which is activated by a finger (152) pressing the knob down, to move the knob closer to plunger (146). Spring (150) is configured to return knob (151) back to a normal position when the finger pressure (152) is released.

The magnetic attraction force between plunger (104) and the ferromagnetic insert provides about 0.40-0.60 Newton. The diameter of the gas port is typically between 0.5 to 1 mm.

Dispensing unit 200A may be used for dispensing air freshener liquids when it desirable to achieve a Sauter D[4,3] mean droplet size of from 20 µm to 60 µM, or in particular from 20 µm to 50 µm, and especially from 25 µm to 35 µm. The desirable pressure at the nozzle should be from 8 to 30 bar and preferably from 15 to 25 bar but typically less than 40 or 30 bar. The pressure may be configured by properly selecting the pressure amplification of the pistons and the liquefied gas.

The spray system may be used for dispensing cosmetic compositions include hair sprays, body sprays, deodorants, antiperspirants, and perfumes. Body sprays and hair are particularly suitable as they require small droplet size.

High flow rates, for example from 0.1 g/s to 1.0 g/s, and, in particular, from 0.2/s to 0.6 30 g/s, can be achieved, while still maintaining good spray quality. Spray quality may be defined by the size of the droplets and droplet size distribution of said droplets. For many applications, it is desirable to achieve a Sauter D[4,3] mean droplet size of from 7 µm to 60 µm, in particular from 10 µm to 50 µm, and especially from 15 µm to 35 µm. It is further preferred that for each of the Sauter D[4,3] preferred ranges indicated above, that the Sauter D[3,2] mean droplet size is also within the same range. The median volume droplet size (Sauter D[v,0.5]) and it is preferred that this value is from 7 µm to 60 µm, in particular from 10 µm to 50 µm, and especially from 15 van to 35 µm. With regard to the narrowness of the droplet size distribution, it is preferred that the gap between the Sauter D[v,0.1] value and the Sauter D[v,0.9] value is 50 microns or less, more preferably 45 microns or less, and especially 40 microns or less.

Handheld aerosol/spray system according to the present invention may have a product volume of at least 30, 60 or 90 ml, but less than 1000, 800 or 600.

Figure 3:
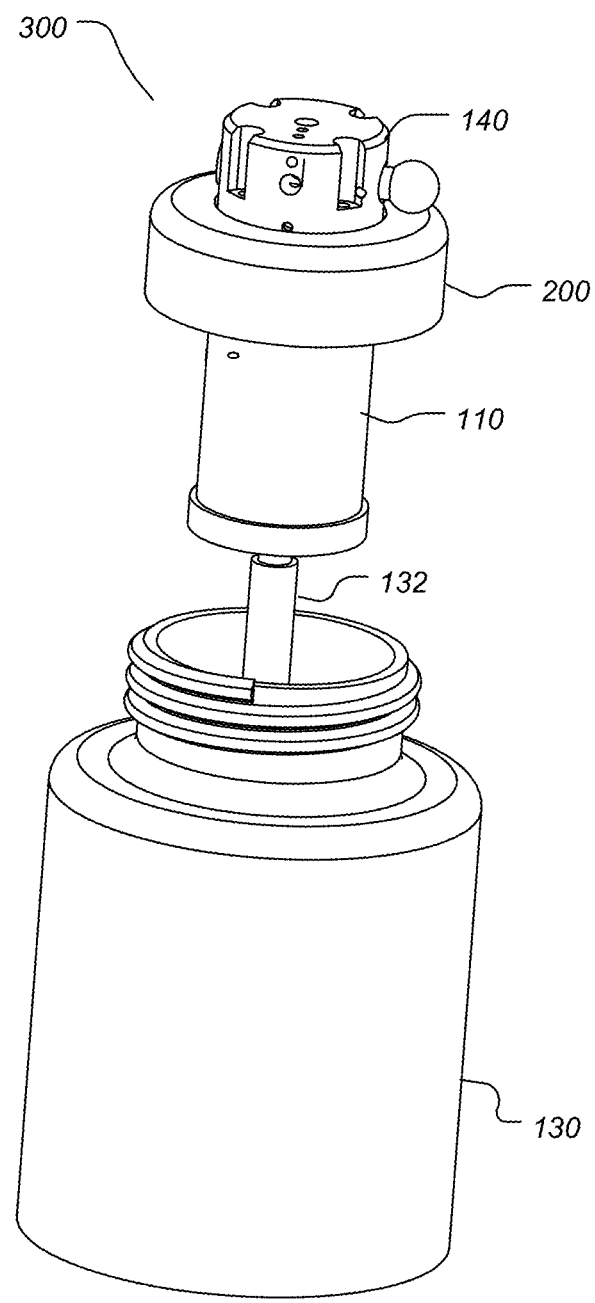
FIG. 3 is a simplified exploded view of certain pressure-multiplying dispensing system parts which include a fluid container.

FIG. 3 illustrates an exploded view of an exemplary embodiment of dispensing unit (300) which includes a pressure multiplying pump (110), a fluid container (130), a diptube (132) and a locknut (200) for connecting the pump (110) to container (130).

In one embodiment container (130) includes a bottom face that moves up toward the pump (110) due to vacuum resulting from the discharge of the container content. Such a configuration is described in U.S. Pat. No. 8,499,970, the entirety of which is hereby incorporated by reference.

FIG. 3A illustrates a cross sectional view of dispensing unit (300) having a housing (160) which includes a pressure multiplying pump (110) and a gas compartment (120). The dispensing unit further includes a control valve (140) that is attached to housing. Housing (160) and the valve unit (140) include a first passageway (143) connecting gas compartment (120) to the valve unit (140) and a second passageway (119) connecting fluid container to the nozzle (115).

Pressure multiplying pump (110) comprising a stepped cylinder bore (111) and reciprocating piston member (112) which includes a pair of axially-connected pistons (112A) and (1128). The pistons are arranged to slide along the axis of the cylinders (111A) and (111B) while maintaining a hermetically tight sealing interference under pressure. This arrangement is configured to multiply the gas pressure as described earlier in relation to dispensing unit (100).

The diameter of first piston (112A) is 34.92 mm and the diameter of the second piston (112B) is 17.46 mm. Piston (112A) is in pressure communication relationship with a source of gas pressure through the valve (140) and piston (112B) is fluid communication with the liquid to be dispensed. The ratio of the area of the piston (112A) and (112B) is 4. In this way, the pressure transmitted to the fluid may be 4 times greater than the gas pressure applied to piston (112A).

Each piston is provided with a flexible skirt-like lip seal that is oriented to expand against the cylinder wall under pressure.

The displacement of piston (111) is 4 mm such that the volume of the liquid that is displaced upon each stroke of the piston is an arithmetic product of the area of the small piston (112B) and its travel. The embodiment described herein displaces a volume of 0.619 mL.

The displacement and the diameter of the piston may be configured to displace a larger or smaller volume. Typically in personal care or household application the volume is 0.2, 0.3, 0.4, 0.5, 0.7, 0.8, or 1, 2 mL, but generally less than 4 mL. The diameter of the larger piston (112A) is less than 50 mm but greater than 10 mm, 20 mm, 30 mm, or 40 mm. High volume reduces the number of actuations which may be preferred in some application or by some users. For example, when applying hairsprays or deodorants in a continuous manner.

The ratio between the diameters of piston (112A) and piston (112B) may be selected according to the consumer preference or the application. Typically the ratio is greater than 1, 2, 3, 4, or 5, but generally smaller than 10.

The pump includes a gas compartment (120) which contains 5 gm of liquefied gas Dymel™ HFC-152A to dispense 100 mL at about 20 bar of pressure. Gas compartment (120) may contain 6, 7, 8, 9, and 10 grams of liquefied gas to dispense higher volume proportionally. A blend of two or more liquefied gases may also be used, such as a blend of HF0-1234ze and Ethane or HF0-1234ze and Dymel™ HFC-152a. Gas compartment (120) contains gas under vapor pressure. Gas compartment (120) will have a sufficient strength to safely withstand the vapor pressure of the selected gas at 50° C. The structural stress of gas compartment may be analyzed and optimized using the Finite Element Analysis computation code available from Ansys Inc., Canonsburg, Pa., USA. Plastic material such as PET may be selected to minimize permeation of the gas through the wall. The wall thickness of gas compartment (120) is about from 1.0 to 2.5 mm. Structural ribs may be provided to enhance the strength of gas compartment (120). Preferably the wall thickness of housing (160) is as uniform as possible.

Control valve (140) is configured to connect gas pressure from compartment (120) to the cylinder (111A) or to discharge gas pressure from the cylinder (111A) to the atmosphere. Control valve (140) comprises a hermetically sealed enclosure (149) which includes a gas inlet orifice (143A), a gas exhaust orifice (141A) and a passageway (142) to cylinder (111A). Control valve (140) includes a rocker arm (145) that selectively opens inlet orifice (143A) and closes exhaust orifice (141A) or oppositely, closes inlet orifice (143A) and opens exhaust orifice (141A). The rocker atm (145) makes small rotational movement about a pivot (151) to open one orifice and close the second orifice. The rocker arm is shown separately in FIG. 3C. It can be seen that rocker arm (145) includes two sealing members (148), (147), a pivot hole (151), a push knob (152), and an o-ring (146).

The sealing members (147), (148) are made from soft elastomeric material such as Silicon rubber, FKM or EPDM which have a hardness value of 60, 70, 80 or 90 Shore Durometer A. The sealing member may be over-molded as an integral part of the rocker arm (145).

FIG. 3B illustrates dispensing unit (300) when valve (140) is in a closed or normal position. Rocker arm is normally biased by a spring (150) to rotate in the clockwise direction. In this way gas inlet orifice (143A) is closed and exhaust orifice (141A) is open to the atmosphere. In the normal position cylinder (111A) is vented to the atmosphere and piston (112) is forced by a spring (117) to the proximal end of the piston travel. Referring back to FIG. 3A it can be seen that when control valve (140) is pressed by a finger (112) (or the like) rocker arm (145) rotates in the counterclockwise direction to close the exhaust orifice (141A) and open the pressure orifice (143A). In this position gas flows to the cylinder through passageway (142) and piston (112) moves from the proximal to the distal end of the travel. This movement displaces the fluid through 30 the dispensing nozzle (115) as indicated by the arrow marked "Fluid Flow". It can be seen that check valve (113) closes and check valve (114) opens thereby restricting the flow of fluid to the dispensing nozzle.

Gas compartment contains liquefied gas HFC-152a which maintains a constant pressure of about 5 bar at 21° C. The pressure that is transmitted to the fluid is multiplied by the ratio of the 5 areas of the pistons (112A) and (112B), which is approximately 4. The pressure that is applied to the fluid is therefore about 20 bar, 4 times higher than the gas pressure. The pressure is measured when the flow through (115) nozzle is fully restricted. When the nozzle is open the dynamic pressure may be about 30 percent lower. Actual pressure also depends on fluid viscosity and the force of spring (117). These parameters and the ratio between the areas of pistons (112A) and (112B) may be configured to achieve the desirable pressure and spray characteristics in accordance with the present invention.

Spring (150) will produce force that is sufficient to shut the opening of the gas nozzle (143A) at elevated temperature of 60° C. when the gas vapor pressure is about 12 bar. The diameter of orifice (143A) is 0.5, 0.7, or 1 mm. Sealing member is configured to apply less than 2 Newton to seal nozzle (143A). Preferably the spring force will apply about 20%, 30% or 40% higher force to safely shut the gas orifice.

Figure 3D:
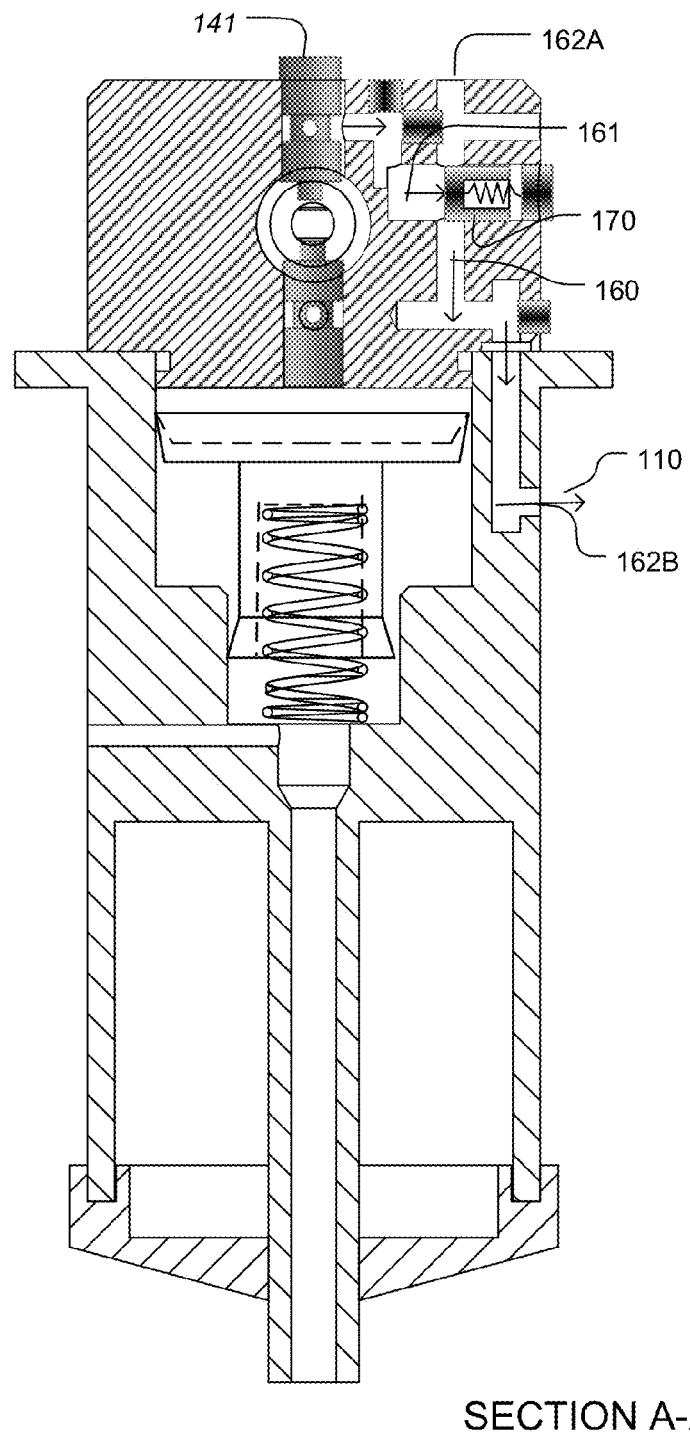
FIG. 3D is a side view in a perpendicular direction relative to the view shown in FIG. 3B.

Dispensing unit (300) further includes a pneumatic means to equalize the pressure in the container as the fluid is being dispensed. FIG. 3D illustrates a cross sectional view of the dispensing unit (300) which is perpendicular to the views in FIG. 3A.

Dispensing unit (300) uses the exhaust gas flow that is discharged from the cylinder (111A) to open a venting channel to the container. Dispensing unit (300) include a venting channel (160) which includes one opening (160A) to the atmosphere and a second opening to the fluid container (160B). Dispensing unit (300) further includes a spring-loaded plunger (170) which normally blocks venting channel (160). Plunger (170) slides in channel (161) which intersects perpendicularly with venting channel (160). Spring-loaded plunger (170) is normally positioned at the intersection between channel (160) and channel (161) to seal the passage of venting channel (160) to the atmosphere. When the gas is discharged through nozzle (141) plunger (170) is displaced from the intersection thereby opening the venting channel (160) to the atmosphere.

FIG. 4 illustrates a cross sectional view of an exemplary embodiment of dispensing unit (600) which includes a pressure multiplying pump (110) and a gas cartridge (120) which includes control valve (140).

Pressure multiplying pump (110) comprised of a cylindrical member (111) with two unequal cylinder bores (111A) and (111B). The first cylinder bore (111A) has a larger diameter than the second cylinder bore (111B). Pump (110) further includes a piston member (112) comprising of two integrally connected pistons (112A) and (112B). The diameter of the first piston (112A) is equal to the diameter of the first cylinder bore (111A) and the diameter of the second piston (112B) is equal to diameter of the second cylinder bore (111B). This arrangement is configured to multiply the gas pressure as described earlier in relation to dispensing unit (100).

FIG. 4C shows an alternative piston member (112) which has uniform wall thickness of about 1 mm and a skirt-like sealing arrangement for each piston (112AS) and (112BS) configured to seal the piston against the cylinder bore under pressure. Such seal is commonly used in a finger-triggered spray pump disclosed for example in U.S. Pat. Nos. 6,050,457, 6,050,457, 4,775,079, 5,353,969 all of which are incorporated here by reference. The area of piston member (112A) is indicated by the letter A and the area of piston member (112B) is indicated by the letter B.

Dispensing unit (600) includes a miniature canister (120) containing liquefied dimethylether (125) which provides a source of pressure to operate the pump. Canister (120) includes a stem valve (140) which controls the release of pressure from the canister to the cylinder (111A).

Stem valve (140) is attached to the opening of the canister (120) by a crimping or by any other process recommended by the manufacturer of such valves. Stem valve that may be used include Lindal Model CA39 F manufactured by Lindal Group Hamburg Germany, or Summit Model SV-77 manufactured by Summit Packaging System Manchester, N.H. USA. Stem valve (140) includes a tube (143) that extends from the inlet opening of stem valve (140) to the gaseous space of the canister. Tube (143) extends to about 1 mm from the base end (120B) of the canister (120). The canister may contain less than 90, 80 or 70 percent gas in liquid state and the balance in gaseous state. The canister is made of metal such as aluminum or plastics, preferably clear plastic such as PET. The wall thickness of the canister is dimensioned to withstand the vapor pressure of the gas at 60° C. The wall thickness may be calculated using the finite element method. Typically, the wall thickness of the canister is about 0.3, 0.4, 0.5, 0.6, 0.7, 0.8, 0.9 mm but less than 3 mm. Due to rapid discharge of gas from the canister to cylinder bore (111A) there will be a slight temperature decrease in the liquefied gas. Temperature decrease reduces the gas pressure. In order to minimize temperature decrease canister (140) may contain a mixture of liquefied gas and water such that the heat capacity of the water will prevent rapid temperature decrease. Typically, the canister contains less than 20, grams of liquefied gas of which the amount of water is 50% or less (by weight of the total composition). However, it should be understood that the volume of the canister and the amount of gas that is contained in the canister is a function of the pressure multiplication and the total amount of the fluid to be dispensed. The total amount of liquefied gas is not limited in the present invention.

Dispensing unit (600) further includes a top cover member (150) which is configured to seal the opening of cylinder (111A). Member (150) includes a circular protrusion (152) that plugs the opening of cylinder (111A) in a pressure-tight sealing engagement. Top cover (150) further includes a socket (151) for securely housing canister (140). Socket (151) is dimensionally configured to allow a sliding interference of canister (120) along the axis of the socket (151). A pair of retaining tabs (not shown in this view) keeps the canister in place within socket (151) in any possible orientation of dispensing unit (600).

Cylinder cover (162) further includes a gas inlet nipple (142) through which the stem valve pressurizes cylinder (111A). Nipple (142) includes an elastomeric washer that seals between the interface between the stem valve and nipple (142). At the normal resting state stem valve (140) is in loose contact engagement with gas inlet nipple (142). Loose contact allows atmospheric pressure communication to cylinder (111A). When the user presses on the canister base (120B), as shown by the illustration of finger (112), stem valve (140) engages with the nipple (142) to seal the inlet of the stem valve (140), subsequently the valve opens and gas pressure is released to cylinder bore (111A). Piston member (112) moves to the distal end of the travel while fluid is displaced through check valve (114) and discharged from dispensing nozzle (115).

Check valve (114) includes a spherical acrylic ball and a 60 degrees valve seat. The ball is normally biased by a spring against the valve seat such that the valve opens when the fluid pressure is greater than 0.3, 0.4, or 0.6 bar but typically less than 1 bar.

When the finger pressure (112) is released, stem valve (140) closes, consequently compression spring (117) displaces piston member (112) back to the proximal end of the travel. Fluid is drawn from the container (not shown) through dip tube (132) and check valve (113) into the cylinder bore (111B). Simultaneously, gas pressure from cylinder (111A) is discharged through the nipple (142) and passage (154) to the atmosphere.

Spring (117) will have the sufficient force to return piston (112) from the distal end of the travel to proximal end of the travel within 100, 200 300 msec. The spring may be configured in accordance with fluid viscosity. Typical compression spring (117) will have a wire diameter of 0.2-1 mm and external diameter from about 3 to 10 mm and be typically less than 30 coils.

FIG. 4C illustrates piston member (112) separately for the purpose of clarity. The diameter of piston (112A) is 13 mm and the diameter of piston (112B) is 8 mm. Thus the area (A) of piston (112A) is equal to 132.7 mm$^2$ and area (B) of piston (112B) is equal to 50.2 mm$^2$. The total amount of liquefied gas that is required to dispense a volume of liquid may be calculated according to the ideal gas law.

Conveniently, the pressure multiplication factor is defined by the letter k according to the following equation:

$$k := \frac{A}{B}$$

Substituting the values of the piston areas A and B:
k=2.641

The pressure that is transmitted to the liquid equals the arithmetic product of the vapor pressure (5 bar) and pressure multiplication factor k.

P(liquid)=5*K=13.2 bar

The mass of liquefied dimethyl ether (DME) that is needed to dispense 1 mL of fluid at 13.2 bar is calculated according to the Ideal Gas Law $$n := \frac{Pvap \cdot V \cdot k}{R \cdot T}$$

n=number of moles of dimethyl ether (DME))
Pvap=5 bar (vapor pressure of DME)
R-=8.314 J joule/K mole (gas constant)
T=293 K (temperature in Kelvin)
V*k is the volumetric displacement of piston 111A to dispense 1 ml of fluid\
n=5.247×10$^4$ mol $$M := 46.7 \frac{gm}{mol}$$

M=molecular weight of dimethyl ether
M:=M·n
weight=0.025·gm

The total weight of dimethyl ether that is required to dispense 1 mL of fluid at 13.2 bar is 0.025 gram or 2.5 percent when calculated as a percentage of total weight of liquid (assuming that the liquid density is 1 gm/ml). In comparison, the amount of dimethyl ether in propellant-based aerosol is 30, 40 or 50 percent.

FIG. 4A and FIG. 4B illustrate enlarged cross sectional views of atomizing nozzle shown as Detail-B in FIG. 4. For clarity FIG. 4B illustrates a partial sectional view of top cover (150) without the nozzle insert (36) and FIG. 4A illustrates a partial sectional view of top cover (150) with the nozzle insert (36).

As illustrated in FIG. 4B, plug-shaped insert post (26) is disposed axis-symmetrically with fluid supply chamber (32). Insert post (26) preferably has a substantially planar end surface (28) adjacent its distal end has generally circular shaped. Insert post (26) can be a separate structure which may be attached to top cover (150) by a mechanical means (e.g., threaded, press fit or the like), but preferably he integrally formed with top cover (150) for simplicity of manufacture (such as by injection molding). Supply chamber (32) generally forms an annulus which is bounded by post surface (30) and inside wall (34). Preferably, supply chamber (32) is adjacent to and in fluid communication with feed tube (23) to initially receive fluid from the storage container.

FIG. 4D and FIG. 4E illustrate an exploded view and a perspective view that best shows the interconnection between external components of dispensing unit (600). As illustrated dispensing unit (600) comprising a cylinder body (110), a top cover (150) and a fluid connection member (23).

Top cover (150) includes a circular protrusion (152) configured to plug and seal cylinder bore (111A). Top cover (150) further includes a socket (32) which providing housing for spray nozzle insert (36). Top cover (150) further includes an inlet bore (70) for insertion of the upper end (23A) of fluid supply member (23). Fluid supply member (23) includes an internal fluid passage (23B) for supplying fluid to the nozzle chamber (32). The diameter of fluid passage is typically 1, 2, 3 or 4 mm and its wall thickness is generally between 0.5 to 3 mm. The upper end of fluid supply member (23) may have thinner wall to allow certain radial expansion of section (23A) toward the inner wall of inlet bore (70) under fluid pressure. Top cover (150) further includes a spring-loaded check valve within housing (20) which provides a venting passage to the fluid container. Such venting passage serves to prevent vacuum buildup in the container as fluid being depleted. The venting check valve opens when the pressure differential between the interior of the container and the ambient pressure is greater than 20, 30 or 40 kPa 40k Pa. Top cover (150) further includes a socket (151) for storing gas canister (120). Socket (151) includes a pair of latching tabs (153) that retains canister (120) in any orientation of dispensing unit (600).

Fluid supply member (23) connects to the cylinder body through a ring (23B) that diametrically fits over the lower section (15) of cylinder body (110) to create a hermetically sealed fluid passage between section (15) and fluid supply member (23B).

FIG. 4E illustrates a perspective view of dispensing unit (600) which includes a locknut (160) configured to connect dispensing unit (600) with fluid container (not shown). Locknut (160) includes a soft gasket which serves to hermetic seal the interface of dispensing unit and the container. Universal S.P.I neck finish specification for standard closure with nominal diameter ranging from 13 mm to 120 mm may be used.

All pump components are provided of appropriate size and material to effectively create a seal therebetween when assembled. In this way there will be no gas or fluid leak between mating surfaces when the dispenser is pressurized or at rest. Although it is preferred that fluid or gas connection are sealed by simple frictional interaction, it will be understood that alternate means such as adhesive connections, ultrasonic welding, tapered locking or o-ring connection may be used.

Figure 4F:
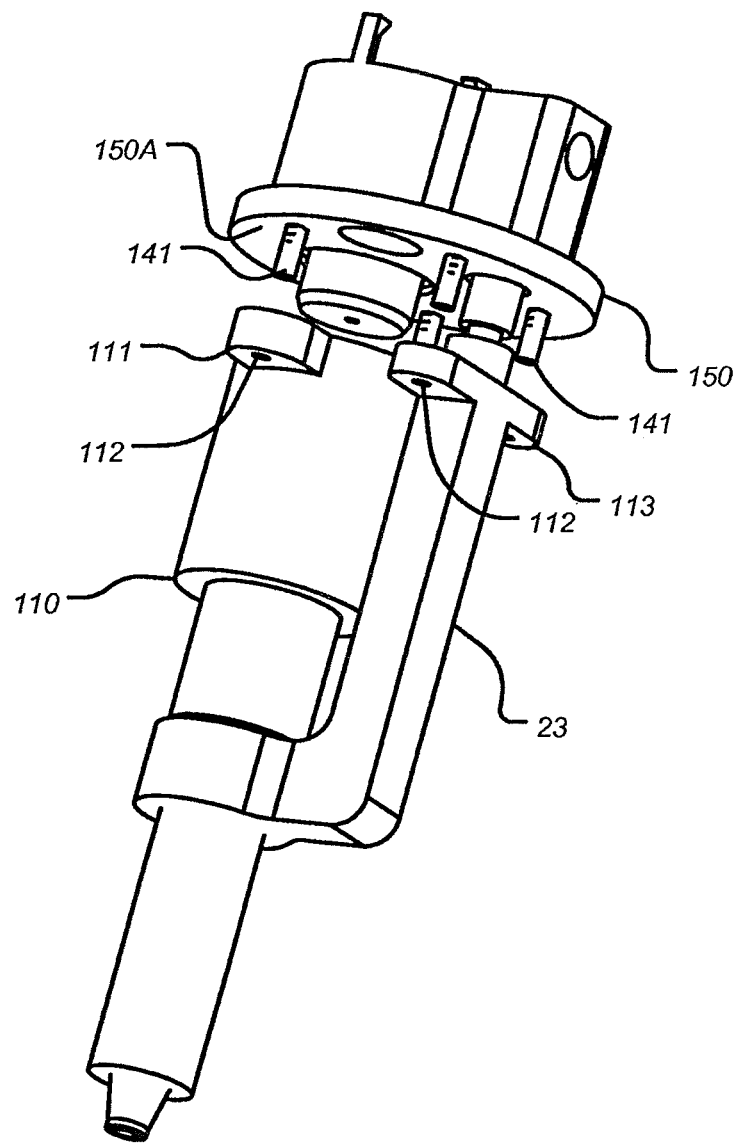
FIG. 4F is a simplified illustration showing of an attachment method of cylinder body and top cover system in accordance with certain embodiments of the invention.

FIG. 4F illustrates an attachment method of cylinder body (110) and top cover (150). It can be seem that top cover (150) includes four protruding bosses (141) each having a diameter of 3 mm and extending perpendicularly from the surface (150A) of top cover (150). Cylinder body includes two ears, the first ear (111) is visible and the second is at the far side and not visible in this view. Each ear includes a pilot hole (112) with oversized diameter relative to the bosses (141). Similarly, fluid passage (23) includes two ears (113) with similar pilot holes. When assembled, cylinder body and top cover are engages such that the four bosses (141) slip fit into pilot holes (112) and (113). Bosses (141) are extended 3 or 4 mm beyond the pilot holes to allow for a thermoplastic staking punch to compress the extended end of the bosses. The stacking process creates radial expansion of the bosses which results in a permanent joint.

Figure 5:
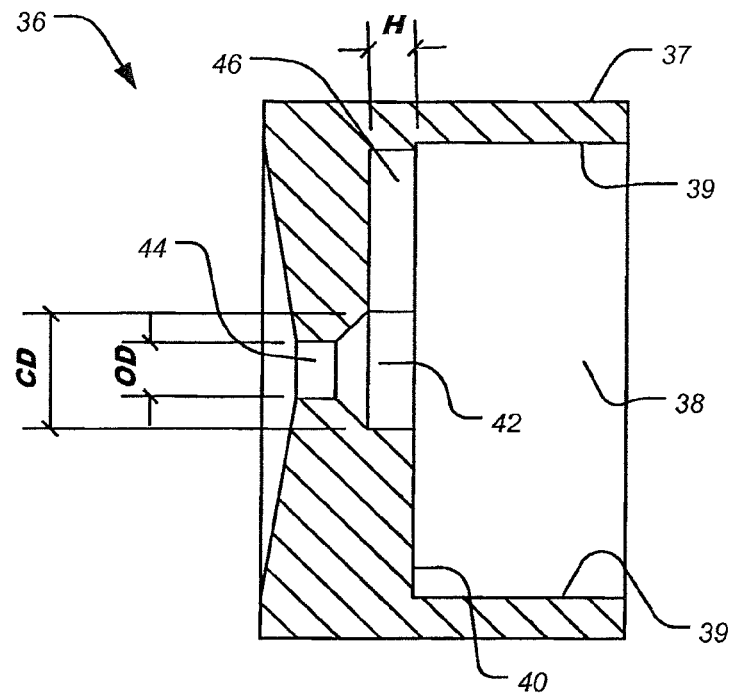
FIG. 5 is a detail view which illustrates nozzle insert in a side view.
Figure 5A:
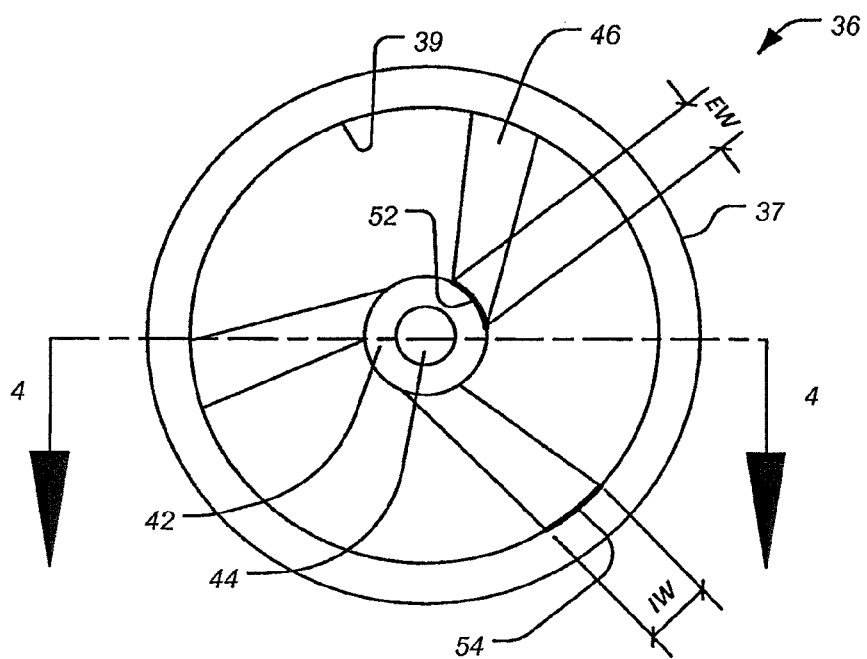
FIG. 5A is a detail view illustrate nozzle insert in a frontal view.

FIG. 5 and FIG. 5A, illustrate nozzle insert (36) in a side frontal and views respectively. It can be seen that the nozzle (36) has a cup-shaped cavity (38) with a cavity surface (39) and an end face (40). Located adjacent to end face (40) and generally concentric with the centerline of (38) is swirl chamber (42), illustrated with a chamber diameter CD. Swirl chamber (42) preferably has a generally conical shape for enhancement of flow efficiency.

A discharge orifice (44) having a predetermined orifice diameter (OD) is preferably located adjacent to and generally concentric with swirl chamber (42). Discharge orifice (44) thereby provides fluid communication between swirl chamber (42) and the ambient environment. As illustrated in FIG. 4E plurality of grooves (46) are disposed on end face (40) extending generally radially inward from cavity surface (39) to conical swirl chamber (42). In a preferred embodiment, each groove (46) connects generally tangentially with swirl chamber (42) and nozzle insert (36) has at least two spaced grooves (46). In the embodiment shown, nozzle insert (36) has three grooves (46) disposed in an equally spaced circular array about swirl chamber (42).

Referring back to FIG. 4A and FIG. 4B it can be seen that the inside wall (34) of supply chamber (32) is preferably sized to receive and frictionally retain nozzle insert (36). Preferably, the surfaces of inside wall (34) and insert surface (37) are sized such that when assembled in contact with each other, they will create an effective seal and there will be generally no liquid flow between the surfaces at 30 bar of pressure.

Nozzle insert (36) is fully assembled with inside wall (34) of top cover (150) such that end surface (28) and end face (40) are in contact, and forming a supply annular passage (50). Annular supply passage (50) is preferably fawned between cavity surface (39) and post surface (30), and extends along at least a portion of the length of cavity surface (39) such that annular supply passage (50) is in fluid communication with both supply chamber (32) and one or more contiguous vanes (48).

Referring back to FIG. 4A and FIG. 4B, as well as FIG. 5 and FIG. 5A, as illustrated in FIG. 4A and FIG. 4B, vanes (48) are defined by the surface (28) of insert post (26) and grooves (46) (FIG. 5A) of insert (21). Each vane (48) has a resulting width W and height H which, in turn, defines a vane cross sectional area A in accordance with the equation:

$$A = W*H$$

Thus, the individual vane exit area EA of each vane exit (52) is the arithmetic product of exit width EW of that vane and height H, while the individual vane inlet area IA of each vane inlet (54) is similarly the arithmetic product of height H and the inlet width IW. For clarity inlet (54) the exit (52) arc shown in the illustration by a thicker line. The cumulative vane inlet area for an atomizing is the summation of the individual vane inlet areas IA while similarly the cumulative vane exit area for an atomizing nozzle is the summation of the individual vane exit areas EA.

Preferred vanes (48) will feature a continuously inwardly decreasing width so that EW is generally less than IW while height H is generally constant over the length of each vane (48). Because the height H is preferably maintained generally constant over the radial length of vane (48), the ratio of the vane exit area EA to vane inlet area IA is generally equal to the ratio of the vane exit width KW to vane inlet width IW. Consequently, both ratios preferably define the narrowing conformation of each vane (48). This narrowing conformation preferably provides a continuously accelerating liquid flow within each vane (48) as the liquid traverses each vane (48) in a direction from supply chamber (32) toward swirl chamber (42).

Although it is preferable that the width of each vane (48) continuously decreases inwardly from cavity surface (39), the spray characteristics of liquid dispensed from nozzles are generally insensitive to the amount of decrease in the vane width W. Thus, the ratio of the vane exit width EW to the vane inlet width IW, and likewise the ratio of vane exit area EA to the vane inlet area IA (if vane height is constant), may vary in a range from about 0.10 to about 1.0.

The proper dimensioning of the cross sectional exit area EA of vanes (48) in cooperation with the proper sizing of chamber diameter CD or orifice diameter OD is critical to achieving the spray characteristics. The Sauter Mean Diameter of a given spray generally decreases according to the following equation, and as graphically illustrated in FIG. 6:

$$SMD = 44.6 - 57.1*(CD*EA)$$

Where SMD=Sauter Mean Diameter (microns)
CD=Chamber diameter for values generally in a range of between about 0.5 mm and about 1.5 mm EA=Individual vane exit area for values generally in the range of between about 0.02 mm$^2$ and about 0.07 mm$^2$.

Figure 6:
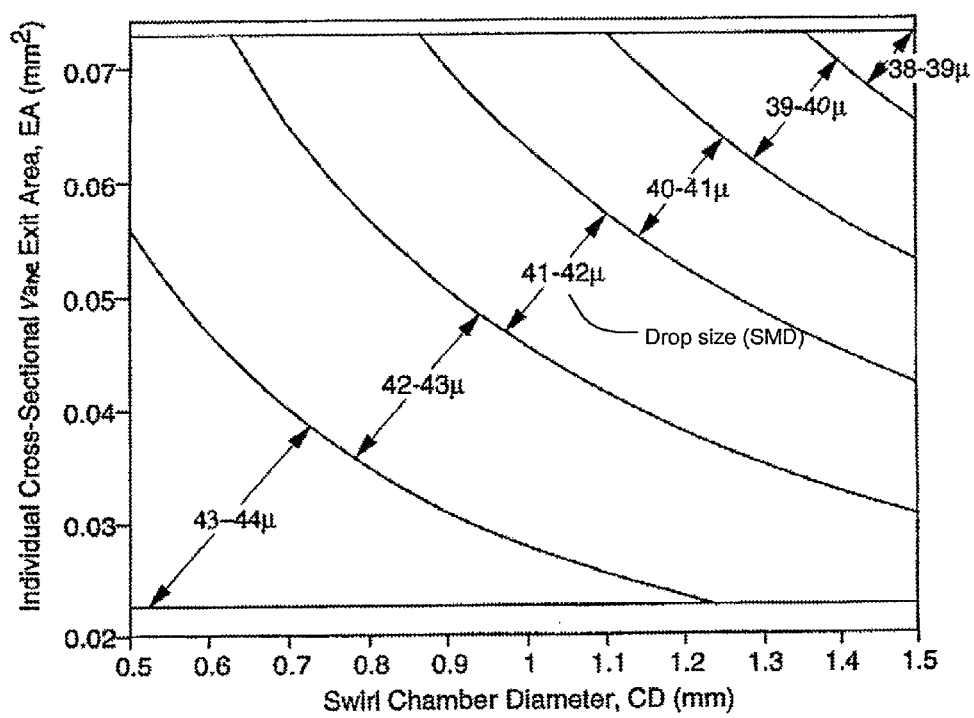
FIG. 6 is a graphic illustration showing the relation between the diameter of the swirl chamber, the droplet size and the cross sectional vane exit in accordance with certain embodiments of the invention.

Although FIG. 6 indicates a generally decreasing particle size as individual vane exit area EA and/or chamber diameter CD increase, data generally indicates that the Sauter Mean Diameter of a resulting spray was found to generally increase if the individual vane exit area EA is about 0.12 mm$^2$ and chamber diameter CD is about 2.0 mm.

Based on the foregoing relationships, the preferred embodiments will have a cumulative vane exit area (i.e., a summation of the individual vane exit areas EA) in a range of between about 0.18 mm$^2$ and about 0.36 mm$^2$ and generally a chamber diameter CD in a range of between about 1.3 mm and about 2.0 mm, and most preferably the chamber diameter CD being in a range of between about 1.4 mm and about 1.5 mm. It has been suggested by U.S. Pat. No. 5,711,488 that such embodiments will generally produce a spray being in the range of between about 38 microns to about 43 microns with a liquid pressure being in the range of between about 11 bar to about 14 bar. U.S. Pat. No. 5,711,488 is hereby incorporated by reference.

In operation, liquid product is provided from a container through feed tube (23) under pressure created by the pressure-multiplying pump. The fluid, upon exiting feed tube (23) enters supply chamber (32) whereupon it enters supply annular passage (50). The pressurized liquid then passes through supply annular passage (50) and is directed into the plurality of vanes (48). Although it is preferred that feed tube (23), supply chamber (32) and supply annular passage (50) cooperate to transport the liquid from the container to the plurality of vanes (48). Preferably, the liquid is continuously accelerated by the decreasing cross sectional area A of each vane (48) which directs the liquid radially inward toward swirl chamber (42). The accelerated liquid preferably exits the vanes (48) generally tangentially into swirl chamber (42), and the rotational energy imparted to the liquid by each vane (48) and the tangential movement into swirl chamber (42) generally creates a low pressure region adjacent the center of swirl chamber (42). This low pressure region will tend to cause ambient air or gas to penetrate into the core of swirl chamber (42). The liquid then exits swirl chamber (42) as a thin liquid film (surrounding aforementioned air core) and is directed through discharge orifice (44) to the ambient environment. Upon discharge, inherent instabilities in the liquid film cause the liquid to break into ligaments and then discrete particles or droplets, thus forming an atomized spray.

Figure 7:
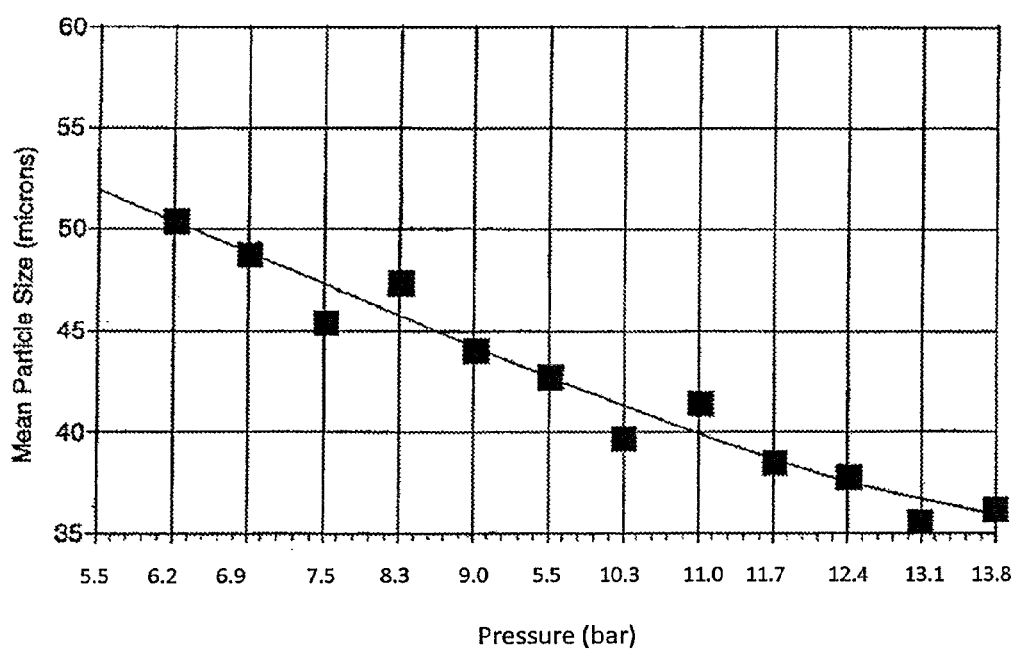
FIG. 7 is a graphic illustration showing the relation between pressure and the droplet size I 0 in accordance with certain embodiments of the invention.

As illustrated in FIG. 7, the preferred embodiment of the present invention generates an atomized spray of liquid particles or droplets having a mean particle size of about 36 microns at a fluid pressure of around 13.8 bar when used to dispense a fluid having a viscosity of about 10 centipoises. In one embodiment the diameter of the swirl chamber is 1.5 mm, the orifice diameter is 340 micron, and the cumulative vane exit area is about 0.9 mm.

While the structure of the nozzle is not intended to be limited to the dispensing of any specific product or category of products, it is recognized that the structure of the spray nozzle which includes the pressure multiplying pump is particularly efficient and applicable for the dispensing, at pressures from about 11 bar to 30 bar, of liquid products having a viscosity, density, and surface tension generally about 10 centipoise, 25 dynes per centimeter respectively with disregard to the application. The structure of the present invention may be used in for dispensing a cosmetic spray, household, industrial spray or the like. It will be understood by one skilled in the art, however, that deviation from these values for appropriate different applications and/or for dispensing of various liquids and viscosities should be possible without affecting the spray characteristics of the present invention. For example, the viscosity of the liquid to be dispensed may vary from about 5 cps to 20 cps without deviating from the scope of this invention.

The foregoing description of the preferred embodiments of the invention has been presented for purposes of illustration and description. It is not intended to be exhaustive or to limit the invention to the precise form disclosed. Modifications or variations are possible and contemplated in light of the above teachings by those skilled in the art, and the embodiments discussed were chosen and described in order to best illustrate the principles of the invention and its practical application, and indeed to thereby enable utilization of the invention in various embodiments and with various modifications as are suited to the particular use contemplated. It is intended that the scope of the invention be defined by the claims appended hereto.

What is claimed is:

1. A hand held hydraulic atomization device for dispensing fluid droplets of a liquid into the atmosphere through a discharge orifice, the device comprising:
    a fluid container for storing the liquid to be dispensed through the discharge orifice;
    a gas container for storing a liquefied gas having a predetermined gas pressure, and in an amount predetermined to be sufficient to dispense the fluid liquid in the container;
    a pressure-multiplying piston pump having a piston member and configured to receive the gas from the gas container, multiplying the pressure of the gas and transmitting the multiplied gas pressure to a portion of the liquid in the fluid container to be dispensed;
    a swirl chamber receiving the pressurized liquid to be dispensed and inducing a spinning motion to the pressurized liquid prior to dispensing through the discharge orifice; and
    a control valve operable to control flow of gas from the gas container to the pressure-multiplying piston pump, and the control valve releasing the pressurized portion of the liquid to the swirl chamber and into the atmosphere through the discharge orifice in the form of an atomized spray having Sauter D, [4,3] mean droplet size from 20 μm to 60 μm.

2. The device of claim 1, wherein the pressure-multiplying pump further comprises:
    a cylindrical member comprising:
        a first body section with a first bore diameter and a first interior surface, in pressure communication with the liquefied gas pressure;
        a first body section with a first bore diameter and a first interior surface, in pressure communication with the container and the swirl chamber,
        wherein the second bore diameter is smaller than the first bore diameter; and
    a spring-loaded piston member operable to reciprocate within the cylindrical member, comprising:
        a first piston having a first piston diameter substantially equivalent to the first bore diameter and operable to slide axially within the first body section such that, when under applied pressure, a first piston skirt lip of the first piston maintains a hermetically tight sealing interface with the first interior surface of the first body section,
        a second piston having a second piston diameter substantially equivalent to the second bore diameter and operable to slide axially within the second body section such that, when under applied pressure, a second piston skirt lip of the second piston maintains a hermetically tight sealing interface with the second interior surface of the second body section,
        wherein the second piston is connected to the first piston.

3. The device of claim 1, wherein the swirl chamber further comprises at least one radial inlet that is tangential to the circumference of the swirl chamber.

4. The device of claim 2, wherein a ratio between surface areas of the first piston and the second piston is greater than 1.

5. The device of claim 1, wherein the liquefied gas comprises liquefied Hydro-fluorocarbon gas HFC-152a.

6. The device of claim 1, wherein the gas comprises liquefied dimethyl ether (DME).

7. The device of claim 1, wherein the gas comprises an unsaturated fluorocarbon, HF0-1234ze.

8. The device of claim 1, wherein the control valve is a stem valve controlling gas pressure of the gas container.

9. The device of claim 2, wherein the first body section is located proximal to the second body section and wherein actuation of the control valve causes liquefied gas pressure to push the spring-loaded piston member axially in a distal direction within the cylindrical member.

10. The device of claim 1, wherein actuation of the control valve causes a volume discharge of the liquid greater than 0.2 mL.

11. The device of claim 1, wherein the mean droplet size is between 20 and 60 microns when a transmitted liquefied gas pressure on the liquid is between 10 and 30 bar.

12. The device of claim 1, wherein the discharge orifice has a diameter of less than 200 microns.

13. The device of claim 1, wherein a liquid flow rate during operation is between 0.1 grams/sec to 1 gram/sec.

14. The device of claim 4, wherein the ratio is greater than 2.

15. The device of claim 1, wherein a material of the container comprises one of the following thermoplastic materials: High-density-polyethylene (HDPE), post consumer resin (PCR), low-density polyethylene (LDPE), polypropylene (PP), K-Resin Polyvinyl Chloride (PVC), PETG or PET.

16. The device of claim 1 wherein the pressure-multiplying pump generates a pressure between 10 and 50 bar.

17. The device of claim 1 wherein the amount of liquid in the fluid container pressurized by the pressure-multiplying piston pump for dispensing is between 0.282 and 6 ml.

18. The device of claim 1 wherein the gas container also contains a predetermined amount of water for temperature control of the gas.

19. The device of claim 1 wherein the diameter of the discharge orifice is 340 microns.

* * * * *